United States Patent [19]

Austen et al.

[11] Patent Number: 4,593,018

[45] Date of Patent: Jun. 3, 1986

[54] OLIGOPEPTIDE ALDEHYDES USEFUL AS SPECIFIC INHIBITORS OF ENTEROKINASE

[75] Inventors: Brian M. Austen; Steven Cliffe; David Grant; John Hermon-Taylor, all of London, England

[73] Assignee: National Research Development Corp., London, England

[21] Appl. No.: 690,486

[22] PCT Filed: May 4, 1984

[86] PCT No.: PCT/GB84/00152

§ 371 Date: Jan. 7, 1985

§ 102(e) Date: Jan. 7, 1985

[87] PCT Pub. No.: WO84/04301

PCT Pub. Date: Nov. 8, 1984

[30] Foreign Application Priority Data

May 5, 1983 [GB] United Kingdom ............... 8312339

[51] Int. Cl.$^4$ ........................... C07K 7/02; C07K 7/06; C07K 5/08; A61K 37/43
[52] U.S. Cl. ........................... 514/16; 514/17; 514/18; 530/331; 530/330; 530/329
[58] Field of Search ............... 514/16, 17, 18; 260/112.5 R

[56] References Cited

PUBLICATIONS

The Journal of Antibiotics, Jun. (1971), pp. 402–404, vol. 24.
Jones et al, Gut 23, No. 11, 939–943 (1982), "Antiproteinase Chemotherapy of Acute Experimental Pancreatitis Using the Low Molecular Weight Oligopeptide Aldehyde Leupeptin".
Hermon-Taylor et al, Clinica Chimica Acta, 109 (1981), 203–209, "Cleavage of Peptide Hormones by 2-Macroglobulin-Trypsin Complex and Its Relation to the Pathogenesis and Chemotherapy of Acute Pancreatitis".
Abstract of Cliffe et al, "The Selective Inhibition of Enterokinase by Synthetic Peptide Aldehydes Based on the Activation Peptide of Trypsinogen".

Primary Examiner—Delbert R. Phillips
Attorney, Agent, or Firm—Oblon, Fisher, Spivak, McClelland & Maier

[57] ABSTRACT

Compounds of the general formula:

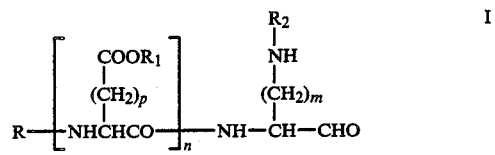

wherein n is an integer from 2 to 6, m is an integer from 2 to 4, p is an integer from 1 to 3, R is H, an amino protecting group conventionally used in peptide chemistry or a solid phase support, $R_1$ is H or a carboxy protecting group conventionally used in peptide chemistry and $R_2$ is H or alkyl or $H_2N-C=NH$ are useful for inhibiting the activity of enterokinases.

10 Claims, No Drawings

OLIGOPEPTIDE ALDEHYDES USEFUL AS SPECIFIC INHIBITORS OF ENTEROKINASE

This invention relates to peptides and is particularly concerned with new oligopeptides having selective inhibitory activity against enterokinase.

Acute necrotising pancreatitis results from runaway activation of digestive enzyme precursors within the pancreas itself. We have shown that the disease is initiated by the displacement of enterokinase from the proximal intestine into the circulation, its carbohydrate dependent uptake by the liver, transfer in catalytically active form to bile the entry of bile-bourne active enterokinase into the pancreatic ducts.

We have now prepared oligopeptide aldehydes which exhibit selective inhibitory activity against the proteinase enterokinase (EC 3.4.21.9) but not against other proteinases of the type inhibited by leupeptin and antipain.

Accordingly the present invention provides a compound of the general formula:

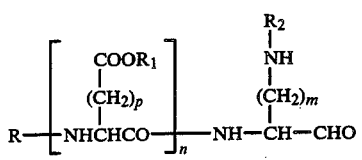

wherein n is an integer from 2 to 6, m is an integer from 2 to 4, p is an integer from 1 to 3, R is H, an amino protecting group conventionally used in peptide chemistry or a solid phase support, $R_1$ is H or a carboxy protecting group conventionally used in peptide chemistry and $R_2$ is H or alkyl or

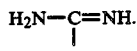

In the compound of formula I, it is preferred that m be 3 and $R_2$ be

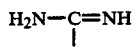

so that the terminal amino aldehyde residue of the oligopeptide is argininal. Further compounds of interest are those in which m is 4 and $R_2$ is H or a $C_1-C_4$ alkyl group e.g. methyl, so that the terminal amino aldehyde residue is lysinal or an N-alkyl lysinal. Higher or lower homologues of argininal or lysinal are also of interest in which the trimethylene or tetramethylene group is replaced by monomethylene or dimethylene.

It is also preferred that p represent 1 so that there is at least one aspartic acid residue present in the block of amino acids linked to the amino aldehyde. There will be at least two amino acid units directly bonded to the terminal amino aldehyde unit. These amino acid units will normally be the same amino acid unit but need not necessarily be the same. For example, although aspartic acid units are preferred, one or more may be replaced for example glutamic acid.

n will be an integer of at least 2 up to 6 and it is preferred that n be 2 or 4 since we have found that the selective inhibitory action of these oligopeptides is at its greatest for the tripeptide and pentapeptide.

It is also preferred that the C-terminal amino aldehyde have L configuration at the α-carbon atom but L configuration is not essential at the other α-carbon atoms in the oligopeptide. D configuration may confer resistance to degradation in vivo.

It is also preferred that the terminal amino aldehyde be L-argininal and that the amino dicarboxylic acids linked to it all be aspartic acid so that the oligopeptide is a polyaspartyl argininal.

The compounds of major interest are the compounds in which the γ-carboxy group in the amino dicarboxylic acid units is unprotected, that is to say $R_1$ is H, as the carboxy protecting groups must be removed to maximise the inhibitory activity. The inhibitory activity is influenced by the presence or absence of the amino protecting group R so that R can be H, a protecting group in the active compounds or a solid phase support. The invention extends to the protected as well as the unprotected forms of the oligopeptides as, as a result of the synthetic methods employed, the oligopeptides are normally first obtained in protected form and the protecting groups are removed in a final stage of synthesis in accordance with conventional methods used in peptide chemistry.

When the terminal amino group is to be protected, it is protected with any of the protecting groups conventionally used, for example tertiary butyloxy carbonyl, benzyloxy carbonyl or acetyl. These groups are of interest primarily because of their stability during the reaction conditions conventionally encountered in peptide synthesis and their ease of removal under acid conditions. However, other amino protecting groups can be used, for example other acyl protecting groups such as simple carboxylic acyl groups or more complex carboxylic acyl groups including oligopeptide residues which arise from peptide synthesis. Solid phase supports for the substitution of the α-$NH_2$ terminus may include polysaccharide based matrices such as Agarose or Dextran or polyacrylamide based matrices.

Similarly, the ω-carboxy group of the amino dicarboxylic acid units require protection during peptide synthesis and again, use may be made of any of the protecting groups conventionally used for the protection of remote carboxy groups which will remain inert during peptide synthesis. Thus, the ω-carboxy group can be protected in the form of an ester, particularly a benzyl ester although other alkyl or aryl ester groups can be used. Other forms of carboxy group protection can be made provided that the protected carboxy group remains inert during peptide synthesis conditions and is readily removable thereafter.

Because the oligopeptides of the invention have a terminal aldehyde residue, traditional solid phase methods of synthesis are not appropriate and a modification of a reduction method known for the synthesis of leupeptin is not appropriate in view of the problems in generating the terminal aldehyde group by reduction in a compound having potentially reducible ω-carboxy groups in the aspartyl residues. Oxidative methods of generating aldehyde groups from the corresponding alcohol have not yet been applied to the synthesis of argininal containing peptides so that it was necessary to adopt a new approach based on fragment condensation. In this method, in addition to the terminal amino and carboxy groups being protected, we also protect the terminal aldehyde group and the quanidinium group if present.

In one of our syntheses, described for the sake of example, for the production of a polyaspartyl argininal, a nitro arginine is first converted into the corresponding arginginal by reduction of the carboxy group and the aldehyde group is immediately protected by reaction with semicarbazide hydrochloride to form the semicarbazone. The desired polyaspartyl peptide is also constructed, protected at the terminal amino group and the ω-carboxy groups and the polyaspartyl material, finally reacted, using an activated ester synthesis, with the N-unprotected nitroargininal semicarbazone. Finally, the various protecting groups are removed to give the polyaspartyl argininal. The reaction scheme is shown in the following schematic drawing where terminal amino groups are protected with tertiary butyloxy carbonyl groups, the ω-carboxy groups are protected as benzyl esters and peptide linkages are formed by reacting N-hydroxysuccinimide esters with N-unprotected amino acids, the terminal carboxy groups being unprotected.

tion. It may also be linked via its α-amino group to a macromolecular carrier such as albumin. Such links may be constructed with cleavable sites so that the molecule may be cleaved at the site of action by digestive proteinases. Oligopeptide I may also be included in the hypaque solution used during endoscopic retrograde pancreatography—a diagnostic procedure that sometimes induces pancreatitis.

The invention also comprises compounds of formula I for use in a method of treatment of the human or animal body by surgery, therapy or of diagnosis practised on the human or animal body, and in particular, for use in the alleviation of the symptoms of pancreatitis by chemoprevention or chemotherapy.

The following example is given to illustrate the invention.

A series of peptide aldehydes were prepared by the general method outlined in the schematic drawing above, to produce a series of polyaspartyl argininals containing 1, 2, 3 or 4 units of aspartic acid. In this example, the following abbreviations are used:

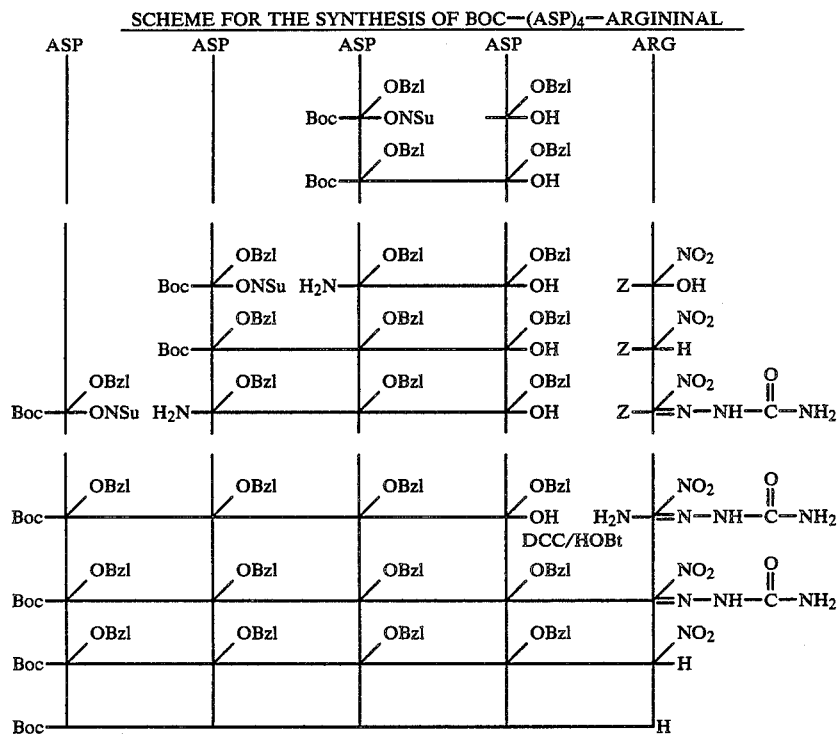

According to a further feature of the invention, we provide a compound of formula I as described above insolubilised on a gel matrix, and a method for the purification of enterokinase comprising bringing a solution of crude enterokinase into contact with such an insolubilised form of a compound to form an insolubilised conjugate of the compound and the enterokinase, separating the insolubilised conjugate from the crude solution and releasing a more pure form of enterokinase from the insolubilised conjugate.

According to a still further feature of the invention, there is provided a pharmaceutical composition comprising an inert pharmaceutically acceptable carrier and, as active ingredient, at least one oligopeptide of formula I as defined above. The oligopeptide I may be formulated, for example, into enteric coated tablets, emulsions, or solutions for oral or parenteral administra- Asp: Aspartic acid
Arg: Arginine
Boc: Tertiarybutyloxycarbonyl
OBzl: Benzyl ester
ONsu: N-hydroxysuccinimide ester
DCC: Dicyclohexylcarbodiimide
HOBt: Tertiary butanol
Z: Benzyloxycarbonyl
TFA: Trifluoroacetic acid
DMF: Dimethylformamide
DIPEA: Diisopropylethylamine
DIBAH: Diisobutylaluminium hydride
TEA: Triethylamine

(a) Boc-Asp(OBzl)-ONSu 19.4 g (60 mmol) Boc-Asp(OBzl) was dissolved in 200 ml dry dioxane, cooled to 4° C. and 7.59 g (66 mmol) N-hydroxysuccinimide followed by 13.66 g (66 mmol) DCC was added. The resulting suspension was stirred at 4° C. for 24 hours. The precipitate was removed by filtration and washed with $CH_2Cl_2$. The filtrate was rotary evaporated to leave an oil, which was taken up in propan-2-ol. Upon leaving in the cold for several days white crystals formed which were filtered, washed with cold propan-2-ol and ether, before being vacuum dessicated. Yield 23.3 g (92.5%) mp 97°–99° C. (lit 103°–104° C., Laufer and Blout, 1967).

(b) Boc-Asp(OBzl)-Asp(OBzl)

To a suspension of 5.57 g (25 mmol) Asp-(OBzl) in 50 ml 1M $NaHCO_3$/dioxane (1:1) was added a solution of 10.5 g (25 mmol) Boc-Asp(OBzl)-ONSu, dissolved in 50 ml dioxane. A further 25 ml $H_2O$ was added and the reaction mixture stirred at 4° C. for 2 h. A small amount of solid remained undissolved and the apparent pH (wet pH paper) had fallen to 6.0. 25 ml 1M $NaHCO_3$ were added and the reaction mixture stirred for a further six hours by which time the reaction had gone to virtual completion as monitored by TLC. The reaction products were poured into 700 ml ice cold water, and cold 2M HCl added to pH 2.5. The resultant oil was extracted once with 200 ml ethyl acetate and twice with 250 ml butyl acetate. The combined organic extracts were washed four times with 100 ml $H_2O$. The organic phase was rotary evaporated and the resultant oil crystallised from toluene-pet ether to yield 8.78 g (66%) mp 88°–91° C. The product comigrated on TLC with that synthesised previously, giving a single ninhydrin positive spot, after exposure to HCl vapour, Rf(B)=0.58, Rf(D)=0.73, Rf(N)=0.43.

(c) Asp(OBzl)-Asp(OBzl). $CF_3COOH$ 7.92 g (15 mmol) Boc-Asp(OBzl)-Asp(OBzl) was taken up in 100 ml $TFA/CH_2Cl_2$ (1:1) and stirred at room temperature for 30 minutes. The solvent was rotary evaporated and the residue triturated with ether to give a white precipitate. Yield 7.49 g (92%). The product gave a single ninhydrin positive spot on TLC Rf(A)=0.75, Rf(B)=0.11, Rf(D)=0.38.

(d) Boc-Asp(OBzl)$_3$

To 6.5 g (12 mmol) $CF_3COOH$. Asp(OBzl)-Asp(OBzl) in 20 ml DMF was added 2.06 ml (12 mmol) DIPEA followed by a solution of 5.29 g (12.6 mmol) Boc-Asp(OBzl)-ONSu in 15 ml DMF. After stirring at room temperature for five hours, TLC analysis showed incomplete removal of the amino component. A further 0.25 g (0.6 mmol) of the active ester was added, and the reaction mixture stirred for a further 3 h; 0.21 ml (1.2 mmol) DIPEA being added for the final 0.5 h. TLC analysis showed complete removal of the amino component, with a very slight amount of active ester remaining. The reaction mixture was diluted with 250 ml ethyl acetate, cooled to 4° C. and washed successively with 2×100 ml 10% (w/v) citric acid, 2×20 ml 5% (w/v) $NaHCO_3$ and 50 ml 0.2M NaCl. The organic phase was dried over $MgSO_4$, rotary evaporated and vacuum dessicated. Attempts to crystallise the product were unsuccessful. It gave one major spot on TLC Rf(B)=0.60, Rf(N)=0.44, Rf(T)=0.14, which was ninhydrin positive after exposure to HCl with a small quantity of a slower moving impurity.

(e) [Asp(OBzl)]$_3$. $CF_3COOH$ 6.62 g (75% of the oily product from (d) was dissolved in 50 ml $TFA/CH_2Cl_2$ (1:1) and stirred for twenty minutes. The solvent was rotary evaporated, the residue triturated with ether and left in the fridge overnight. The resulting white solid was filtered, washed with cold ether and vacuum dessicated over NaOH to yield 6.08 g (8.13 mmol). Single spot on TLC, Rf(A)=0.9, Rf(N)=0.43, Rf(T)=0.10.

(f) Boc-[Asp(OBzl)]$_4$.

To 5.98 g (8 mmol) [Asp(OBzl)]$_3$. $CF_3COOH$ in 20 ml DMF was added 3.70 g (8.8 mmol) Boc-Asp-ONSu followed by 1.38 ml (8.0 mmol) DIPEA. The reaction mixture was stirred at room temperature for 5 hours, when TLC analysis showed complete removal of the amino component. The products were cooled to 4° C., diluted with 250 ml ethyl acetate and washed sequentially with 2×100 ml 10% (w/v) citric acid, 1×50 ml (w/v) $NaHCO_3$ and 50 ml $H_2O$. The organic phase was dried over $MgSO_4$ and rotary evaporated. The residue was taken up in toluene, pet ether added to slight turbidity and the solution left in the fridge over the weekend to give 4.38 g (4.67 mmol) Boc-[Asp(OBzl)]$_4$ soft white crystals, mp 76°–79° C., R(f)N=0.45, Rf(T)=0.17, Rf(W)=0.21.

Evaporation of the mother liquor and recrystallisation from toluene/pet ether gave a second crop 1.71 g, mp 72°–75° C. Total yield 6.1 g (6.5 mmol), 81%. Both crops showed two minor slower running impurities on TLC, but were used without further purification.

(g) Z-Arg(NO$_2$)-semicarbazone

A 250 ml pressure equalising separating funnel was inserted in a three-necked, 500 ml round bottom flask, itself placed in a bath of acetonitrile/dry ice, with a magnetic stirrer. Nitrogen, dried by passing over molecular sieve 4A, entered via a hypodermic needle inserted in a rubber septum (Aldrich). 12.4 g (35 mmol) Z-Arg(NO$_2$) was vacuum dessicated over $P_2O_5$ overnight and then dissolved in 100 ml dry THF under nitrogen and cooled to 10° C. 6.24 g (38.5 mmol) carbonyldiimidazole was added and the suspension stirred at 10° C. until all the solids had dissolved. The solution was then cooled to −42° C. 100 ml 1M-DIBAH in toluene, (Aldrich), was transferred from the reagent bottle to the separating funnel under nitrogen pressure using teflon-tubing connected hypodermic needles as described by Lane and Kramer (1977). The reducing agent was added dropwise to the stirred reaction mixture over 25 minutes, and stirring continued at =42° C. for a further 30 minutes. The reaction was quenched by the slow addition of 250 ml 1.2M-HCl. The resulting suspension was allowed to warm to room temperature. 250 ml 0.6M-HCl and 450 ml $CHCl_3$ were added and the emulsion stirred vigorously for two hours. The organic phase was separated from the aqueous phase, and from an oily precipitate which failed to partition. The organic extract was washed with water, dried over $MgSO_4$ and rotary evaporated to give 2.96 g crude aldehyde, Rf(V)=0.5. To this, dissolved in 8 ml 70% (w/v) aqueous ethanol, was added 1.39 g (17.4 mmol) sodium acetate and 0.97 g (8.7 mmol) semicarbazide HCl; and the reaction mixture heated at 75° C. until all the solids had dissolved. The solution was cooled to 4°

C. and 10 ml water added to give a white suspension which was left in the fridge overnight. The precipitate was centrifuged, washed with cold ethanol and vacuum dessicated to give 1.95 g crude semicarbazone. Recrystallisation from absolute ethanol gave white crystals. Yield 1.733 g (3.93 mmol) 11.2%. mp 107°–109° C., (lit 107°–109° C., Shimizu et al, 1972).

| Elemental analysis Z—Arg(NO$_2$)—semicarbazone. C$_2$H$_5$OH | | | |
|---|---|---|---|
| | C | H | N |
| Calculated | 46.35 | 6.41 | 25.45 |
| Found | 45.24 | 5.80 | 27.15 |

The product gave one spot on TLC which was chlorine-starch/KI and 2, 4, dinitrophenylhydrazine positive, Rf(X)=0.17. (Lit 0.19, Patel and Shultz, 1982), with a small amount of an impurity present at the origin.

(h) Arg(NO$_2$)-semicarbazone

To 1.733 g (3.93 mmol) Z-Arg(NO$_2$)-semicarbazone, dissolved in 8 ml acetic acid was added 20 ml 45% HBr in acetic acid. After stirring at room temperature for thirty minutes the solution was poured into 250 ml dry ether to yield a yellow precipitate. After leaving in the fridge overnight, the precipitate was filtered, washed with ether and recrystallised from methanol. Yield 1.2 g HBr. Arg(NO$_2$)-semicarbazone.

| Elemental analysis: | C | H | N |
|---|---|---|---|
| Calculated | 26.64 | 5.02 | 32.85 |
| Found | 24.27 | 5.43 | 31.50 |

The salt was dissolved in 6 ml water and 0.49 ml (3.52 mmol) TEA added. The solution was left in the fridge overnight to yield a pale green precipitate, which was centrifuged, washed with water and ethyl acetate and vacuum dessicated. Yield 545 mg (2.09 mmol). Arg-(NO$_2$)-semicarbazone, mp 178°–180° C. decomposed (lit decomposed at 186°–188° C., Shimizu et al, 1972).

| Elemental analysis | C | H | N |
|---|---|---|---|
| Calculated | 32.30 | 6.20 | 43.06 |
| Found | 32.26 | 6.18 | 42.11 |

The product gave a single ninhydrin positive spot on TLC and HVPE at pH 6.5 Rf(O)=0.40, Rf(P)=0.52, R(Asp)=+0.52 (predicted +0.64).

(i) Boc-[Asp(OBzl)]$_n$-Arg(NO$_2$)-semicarbazone (n=1, 2, 3, 4)

Boc-[Asp(OBzl)]$_2$, Boc-[Asp(OBzl)]$_3$ and Boc-[Asp(OBzl)]$_4$, 0.525 L mmol of each dissolved in 1 ml DMF, were activated at 4° C. by adding 83 mg (0.575 mmol) HOBt and 120 mg (0.575 mmol) DCC. The resulting suspensions were stirred for 40 minutes at room temperature, filtered and the solid washed with 1 ml DMF. To each of the three filtrates, and to a solution of 0.525 mmol Boc-Asp(OBzl)ONSu in 1 ml DMF, all at 4° C., was added 130 mg (0.5 mmol) aliquots of Arg(NO$_2$)-semicarbazone. The solutions were stirred at 4° C. for 7 hours. A further 12 mg DCC was added to each reaction vessel, and stirring continued at 4° C. for a further 15 hours when TLC analysis showed removal of the amino component. The solutions were filtered, the solid washed with 1 ml DMF and 20 ml of water added to each filtrate to yield oily precipitates, which were vacuum dessicated over P$_2$O$_5$. The resulting solids were recrystallised from propan-2-ol (for n=1) or triturated with EtOAc, a little diethyl ether added and left in the fridge overnight, (for n=2, 3, 4). The solids were centrifuged, washed with cold EtOAc and vacuum dessicated.

| Yields | |
|---|---|
| Boc—Asp(OBzl)—Arg(NO$_2$)—semicarbazone Rf(T) = 0.20 Rf(W) = 0.06 | 142 mg (50%) |
| Boc—[Asp(OBzl)]$_2$—Arg(NO$_2$)—semicarbazone Rf(T) = 0.36 Rf(W) = 0.13 | 253 mg (65%) |
| Boc—[Asp(OBzl)]$_3$—Arg(NO$_2$)—semicarbazone Rf(T) = 0.43 Rf(W) = 0.16 | 270 mg (55%) |
| Boc—[Asp(OBzl)]$_4$—Arg(NO$_2$)—semicarbazone Rf(T) = 0.50 Rf(W) = 0.19 | 318 mg (54%) |

The products gave one ninhydrin, fluorescent and 2, 4 dinitrophenylhydrazine positive spot on TLC with the mobilities given above. Boc-Asp(OBzl)-Arg(NO$_2$)-carbazone showed a minor impurity at the origin.

(j) Boc-[Asp(OBzl)]$_n$-(NO$_2$)-Argininal (n=1, 2, 3, 4)

To 0.15 mmol of the four semicarbazones, dissolved in 1.5 ml MeOH was added 1.5 mmol formaldehyde (0.122 ml 37% (v/v) in H$_2$O) and 1.5 mmol (0.086 ml) glacial acetic acid. For n=3 and n=4 a small precipitate formed which was solubilised by addition of 0.25 ml and 0.5 ml DMF respectively. The solutions were stirred at room temperature; further aliquots of 62 μl formaldehyde and 42 μl glacial acetic acid being added after 2 hours (for n=1, 2, 3, 4) and 7 hours (for n=3, 4). After 24 hours TLC analysis showed complete conversion of the starting materials to faster running components. Approximately 5 ml H$_2$O was added to each solution to yield white suspensions. After cooling in the fridge overnight the suspensions were centrifuged, and the pellets washed twice with water before being dessicated.

| Yields | |
|---|---|
| Boc—Asp(OBzl)—(NO$_2$)Argininal Rf(B) = 0.51 Rf(T) = 0.57 Rf(W) = 0.21 | 25 mg |
| Boc—[Asp(OBzl)]$_2$—(NO$_2$)Argininal Rf(B) = 0.62 Rf(T) = 0.63 Rf(W) = 0.23 | 103 mg |
| Boc—[Asp(OBzl)]$_3$—(NO$_2$)Argininal Rf(B) = 0.66 Rf(T) = 0.67 Rf(W) = 0.24 | 140 mg |
| Boc—[Asp(OBzl)]$_4$—(NO$_2$)Argininal Rf(B) = 0.71 Rf(T) = 0.71 Rf(W) = 0.26 | 169 mg |

The products each gave one ninhydrin (after exposure to HCl vapour), fluorescent and 2, 4 dinitrophenylhydrazine positive spot on TLV with the mobilities given above. Trace impurities at Rf(T)=0.0 and 0.21 were visible in all samples.

(k) Boc-(Asp)$_n$-Arginial (n=1, 2, 3, 4)

The fully protected peptide aldehydes were dissolved in 1.5 ml MeOH to which was added 30 μl glacial acetic acid and 250 μl H$_2$O. The side chain protecting groups were removed by catalytic hydrogenation over 20 mg Pd/charcoal. After 24 hours the catalyst was removed by filtration, the filtrate freezed dried and vacuum dessicated over P$_2$O$_5$.

|  | Yield | % peptide by weight[a] | Asp:Argininal[b] |
|---|---|---|---|
| Boc—Asp—Argininal | 19 mg | 70% | 1.2:1 |
| Boc—(Asp)$_2$—Argininal | 51 mg | 98% | 3.4:1 |
| Boc—(Asp)$_3$—Argininal | 76 mg | 89% | 4.6:1 |
| Boc—(Asp)$_4$—Argininal | 81 mg | 96% | 6.9:1 |

[a] based on the aspartic acid content as determined by amino acid analysis
[b] argininal estimated by quantitative Sakaguchi reaction Alternate synthetic procedures have also been employed. LiAlH$_4$ has been used to reduce CbZ- or Boc-(NO$_2$) L arginine imidazolide and the protecting group removed by treatment with saturated HCl in dioxane. The protected tetraaspartyl peptide mediated DCC coupling instead of with hydroxysuccinimide esters linking Boc(Asp OBZ)$_2$ to (Asp OBZ)$_2$. Removal of O benzyl groups on the aspartyl side chains, and the NO$_2$- protecting group on the guanidine moiety has been achieved by catalytic transfer hydrogenation from ammonium formate in the presence of PdC (5%).

BIOLOGICAL RESULTS

Biological testing was carried out on the polyaspartyl argininal materials prepared as described above without further purification. In order to demonstrate their selective inhibitory action towards enterokinase, comparative tests were carried out between the materials of the invention and leupeptin. Inhibition constants $K_i$ for human and pig enterokinase were calculated using α-N-[$^3$H] acetyl trypsinogen and Gly-(Asp)$_4$-Lys-2-Nap as substrates using linear regression analysis of 1/v against [I] at three substrate concentrations. Inhibition of trypsin catalysed hydrolysis of both these substrates and Bz-Arg-OEt was expressed as the IC$_{50}$, the concentration of inhibitor required to reduce trypsin activity by 50%. The results to activation peptides, four peptides of the invention, leupeptin and p-aminobenzamidine are set out in Tables 1 to 3 below.

TABLE 1
INHIBITION CONSTANTS FOR HUMAN ENTEROKINASE (K$_i$) AND TRYPSIN (IC$_{50}$) WITH Gly—(Asp)$_4$—Lys—2-Nap AS SUBSTRATE

| | Substrate Gly—(Asp)$_4$—Lys—2—Nap | |
|---|---|---|
| Inhibitor | Human Enterokinase (K$_i$) | Trypsin (IC$_{50}$) |
| Boc(Asp)$_1$Argal | 80 ± 5 μM | >500 μM |
| Boc(Asp)$_2$Argal | 0.2 ± 0.05 μM | ~20 μM |
| Boc(Asp)$_3$Argal | 0.1 μM | ~50 μM |
| Boc(Asp)$_4$Argal | 0.055 ± 0.005 μM | ~50 μM |
| Leupeptin | 1.0 μM | 0.175 μM |
| (Asp)$_4$Lys | 100 μM | — |
| Ala—Pro—Phe—(Asp)$_4$Lys | 750 μM | — |

TABLE 2
INHIBITION CONSTANTS FOR HUMAN ENTEROKINASE (K$_i$), PIG ENTEROKINASE (K$_i$) AND TRYPSIN (IC$_{50}$) WITH α-N—[$^3$H] ACETYL TRYPSINOGEN AS SUBSTRATE

| | Substrate α-N—[$^3$H]acetyltrypsinogen | | |
|---|---|---|---|
| Inhibitor | Human Enterokinase (K$_i$) | Pig Enterokinase (K$_i$) | Trypsin (IC$_{50}$) |
| Boc(Asp)$_1$Argal | 50 ± 25 μM | 55 ± 10 μM | >300 μM |
| Boc(Asp)$_2$Argal | 0.01 ± 0.005 μM | 0.05 ± 0.01 μM | >30 μM |
| Boc(Asp)$_3$Argal | 0.02 ± 0.005 μM | 0.035 ± 0.005 μM | >100 μM |
| Boc(Asp)$_4$Argal | 0.01 ± 0.005 μM | 0.02 ± 0.01 μM | >100 μM |
| Leupeptin | 1.0 μM | ≧1.0 μM | 0.35 μM |
| p-aminobenzamidine | ≧50 μM | ≧50 μM | ≦300 μM |

TABLE 3
INHIBITION CONSTANTS FOR TRYPSIN (IC$_{50}$) WITH Bz—Arg—OEt AS SUBSTRATE

| | Substrate Trypsin (IC$_{50}$) | | | | | | |
|---|---|---|---|---|---|---|---|
| | Boc(Asp)$_n$Argal | | | | | | |
| Inhibitor | 1 | 2 | 3 | 4 | Leupeptin | p-aminobenzamidine | (Asp)$_4$Lys |
| Bz—Arg—OEt | N.D. | >500 μM | >750 μM | >750 μM | 2.5 ± 0.5 μM | ≦150 μM | >1500 μM |

The results show the specific inhibitory activity of the invention oligopeptides with respect to enterokinase, particularly of the tetraaspartyl argininal material.

An example of the use of compounds described in formula I as α-NH$_2$ immobilised ligands for the affinity chromatography of mammalian enterokinase is given as follows: Boc(Asp OBZ)$_4$ argininal semicarbazone was treated with 4M HCl/dioxane for 30 min., and evaporated. The precipitated hydrochloride was filtered off, washed with dioxane, and hydrogenated in methanol with Pd/C (5%) for 12 h. at room temperature. The catalyst was filtered off, the deprotected semicarbazone isolated, and incubated (10 mg/μl) with Affi-gel 10 (Bio-Rad, Richmond, Ca., USA) in 0.1M Hepes-NaOH, pH 7.4, containing 10 mM CaCl$_2$ for several hours at 4° C., followed by capping with 1M glycine (pH 8). The aldehyde was regenerated on the affinity matrix by treatment with excess formaldehyde in methanol with 5% acetic acid for 12 h. at room temperature. The affinity matrix was washed with 1M NaCl, and equilibrated in 0.05 Hepes-NaOH (pH 7.6), containing 10 mM CaCl$_2$, and a sample of enterokinase-containing biological fluid applied. The purified enzyme was eluted by lowering the pH of the operational buffer and the addition of EDTA.

We claim:
1. A compound of the general formula:

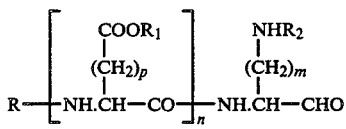

wherein n is an integer from 2 to 6, m is an integer from 2 to 4, p is an integer from 1 to 3, R is H, an amino protecting group conventionally used in peptide chemistry or a solid phase support, $R_1$ is H or a carboxy protecting group conventionally used in peptide chemistry and $R_2$ is H or alkyl or

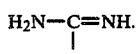

2. A compound according to claim 1 wherein m is 3 and $R_2$ is

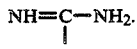

3. A compound according to claim 1 wherein m is 4 and $R_2$ is $CH_3$.

4. A compound according to any one of the preceding claims wherein p is 1 and $R_1$ is H.

5. A compound according to any one of the preceding claims wherein n is 2 or 4.

6. A compound according to any one of the preceding claims wherein R is tertiary butyloxycarbonyl or acetyl.

7. A compound according to claim 1 of the formula:

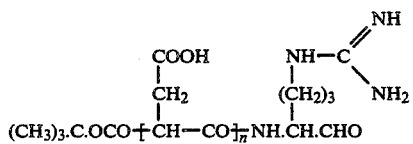

in which n is 2 or 4.

8. A compound according to any one of the preceding claims insolubilised on a gel matrix.

9. A pharmaceutical composition for alleviating the symptoms of pancreatitis comprising an effective amount of a compound according to any one of claims 1 to 7 together with an inert pharmaceutically acceptable carrier or diluent.

10. A method of treatment for alleviating the symptoms of pancreatitis comprising administering to a host in need of such treatment an effective amount of a compound according to any one of claims 1 to 7.

* * * * *

UNITED STATES PATENT AND TRADEMARK OFFICE
CERTIFICATE OF CORRECTION

PATENT NO. : 4,593,018
DATED : JUNE 3, 1986
INVENTOR(S) : BRIAN M. AUSTEN ET AL

It is certified that error appears in the above-identified patent and that said Letters Patent is hereby corrected as shown below:

Please change the structure of Claim 7 from

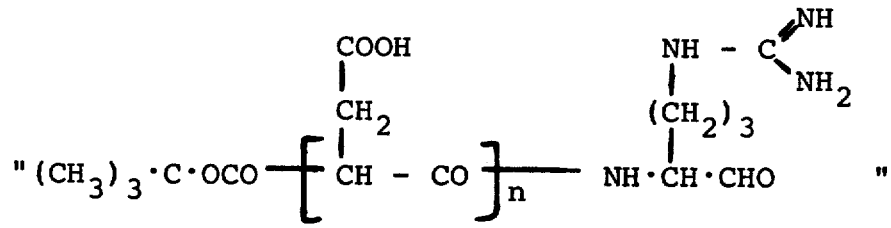

to

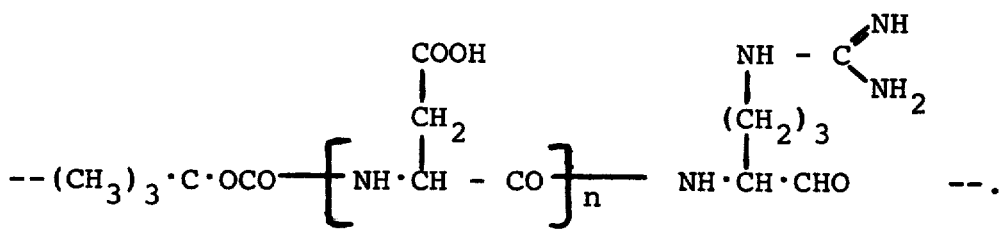

Signed and Sealed this

Fourth Day of November, 1986

[SEAL]

Attest:

DONALD J. QUIGG

*Attesting Officer*     *Commissioner of Patents and Trademarks*